United States Patent
Horne et al.

(10) Patent No.: US 9,233,976 B2
(45) Date of Patent: *Jan. 12, 2016

(54) BERBAMINE DERIVATIVES

(71) Applicant: CITY OF HOPE, Duarte, CA (US)

(72) Inventors: David Horne, Altadena, CA (US); Jun Xie, Monrovia, CA (US); Angela L. Perkins Harki, Minneapolis, MN (US); Richard Jove, Glendora, CA (US); Sangkil Nam, South Pasadena, CA (US); Wendong Huang, Glendora, CA (US); Rongzhen Xu, Hangzhou (CN)

(73) Assignee: CITY OF HOPE, Duarte, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/173,764

(22) Filed: Feb. 5, 2014

(65) Prior Publication Data

US 2014/0155423 A1 Jun. 5, 2014

Related U.S. Application Data

(62) Division of application No. 12/783,535, filed on May 19, 2010, now Pat. No. 8,722,698.

(60) Provisional application No. 61/179,504, filed on May 19, 2009.

(51) Int. Cl.
*C07D 491/147* (2006.01)
*A61K 31/4745* (2006.01)

(52) U.S. Cl.
CPC ........ *C07D 491/147* (2013.01); *A61K 31/4745* (2013.01)

(58) Field of Classification Search
None
See application file for complete search history.

(56) References Cited

U.S. PATENT DOCUMENTS 6,617,335 B1 9/2003 Wang et al.
8,722,698 B2 * 5/2014 Horne et al. .................. 514/279

FOREIGN PATENT DOCUMENTS

CN 101429201 A 5/2009

OTHER PUBLICATIONS

Gong, et al., Chemical Abstract, Zhongguo Yaoke Daxue Xuebao (1991), 22(2), 93-6.
Xie, J., et al., "Berbamine Derivatives: A Novel Class of Compounds for Anti-Leukemia Activity," European Journal of Medicinal Chemistry (2009), doie: 10.1016/j.ejmech.2009.02.018, pp. 1-6.

* cited by examiner

*Primary Examiner* — Zinna Northington Davis
(74) *Attorney, Agent, or Firm* — Perkins Coie LLP; Yingli Wang

(57) ABSTRACT

The invention provides novel berbamine derivatives, and compositions or pharmaceutical compositions thereof. These berbamine derivatives have shown higher potency in killing cancer/tumor cells comparing to berbamine, and can be used in cancer/tumor treatments.

5 Claims, 23 Drawing Sheets

A)

B)

A) Purified recombinant Jak2 protein + ATP ± inhibitors

B)

A)

B)

BERBAMINE DERIVATIVES

PRIORITY STATEMENT

The present application is a divisional of U.S. application Ser. No. 12/783,535, filed May 19, 2010, which claims priority to U.S. Provisional Patent Application No. 61/179,504, filed on May 19, 2009, which is incorporated herein by reference.

FIELD OF THE INVENTION

This invention relates to the field of compounds and pharmaceutical compositions thereof, and methods of using the compounds and pharmaceutical compositions thereof for treating cancer and tumor.

BACKGROUND OF THE INVENTION

Berbamine is a natural product derived from the plant, *Berberis vulgaris*, which has been used extensively in Asia and Europe for the treatment of various ailments. Berbamine is known to possess anticancer properties. Despite the widespread use of berbamine in traditional plant medicines, only a handful of berbamine derivatives have been reported. Therefore, there is a need to synthesize novel berbamine derivatives for potential therapeutic treatments.

SUMMARY OF THE INVENTION

One aspect of the present disclosure relates to berbamine derivatives and pharmaceutical compositions thereof.

Another aspect of the present disclosure relates to a method of treating cancer and tumor using berbamine derivatives and pharmaceutical compositions thereof.

DETAILED DESCRIPTION OF THE INVENTION

Figure 1:
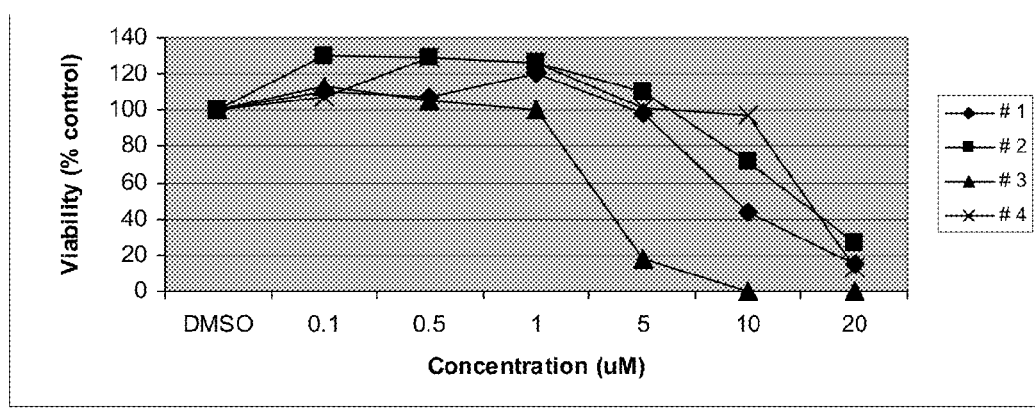
FIG. 1. Viability of DU145 cells treated with BA #1 (diamond), BA #2 (square), BA #3 (triangle) and BA #4 (—X—).
Figure 2:
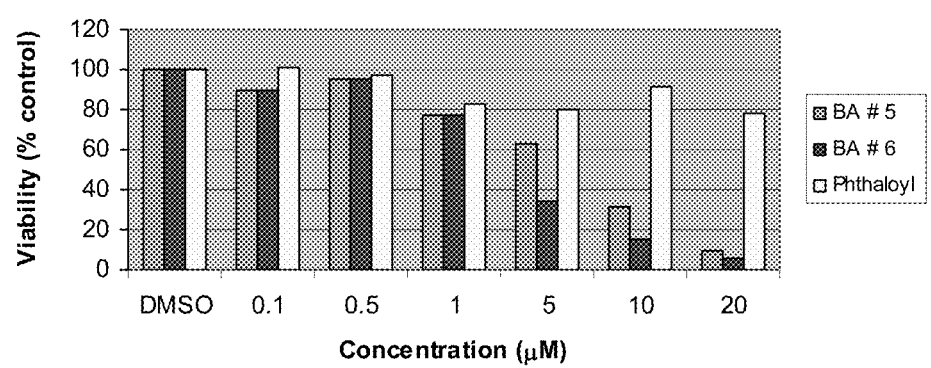
FIG. 2. Viability of DU145 cells treated with BA #5 (grey block), BA #6 (dark block) and phthaloyl derivative (Phthaloyl, white block).
Figure 3:
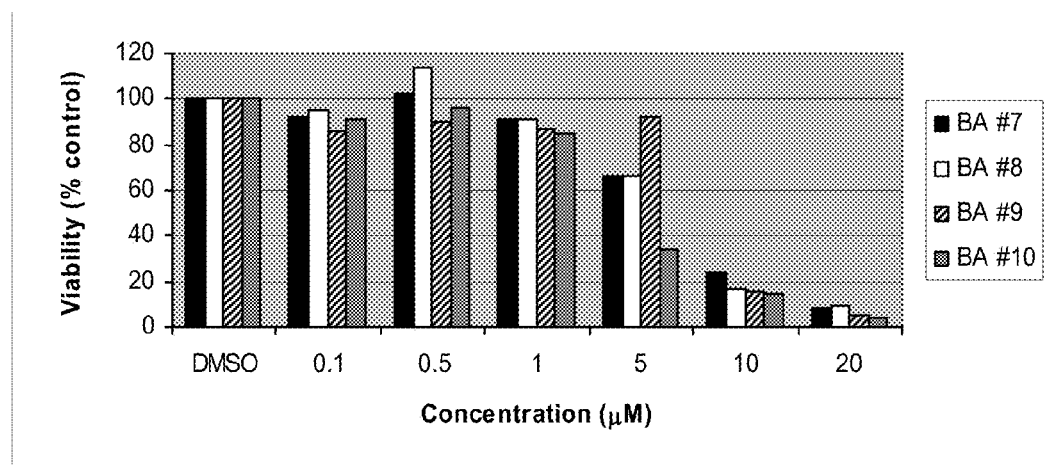
FIG. 3. Viability of DU145 cells treated with BA #7 (dark block), BA #8 (white block), BA #9 (stripe block) and BA #10 (grey block).
Figure 4:
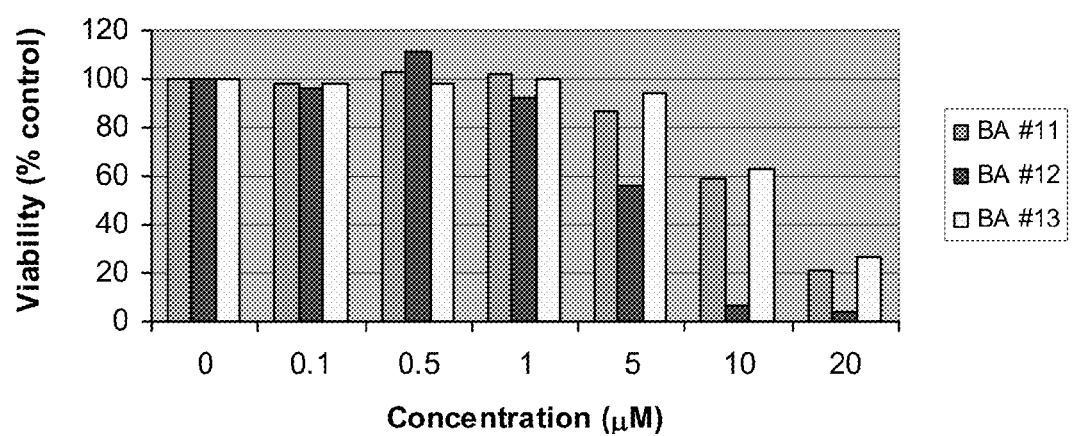
FIG. 4. Viability of DU145 cells treated with BA #11 (grey block), BA #12 (dark block) and BA #13 (white block).
Figure 5:
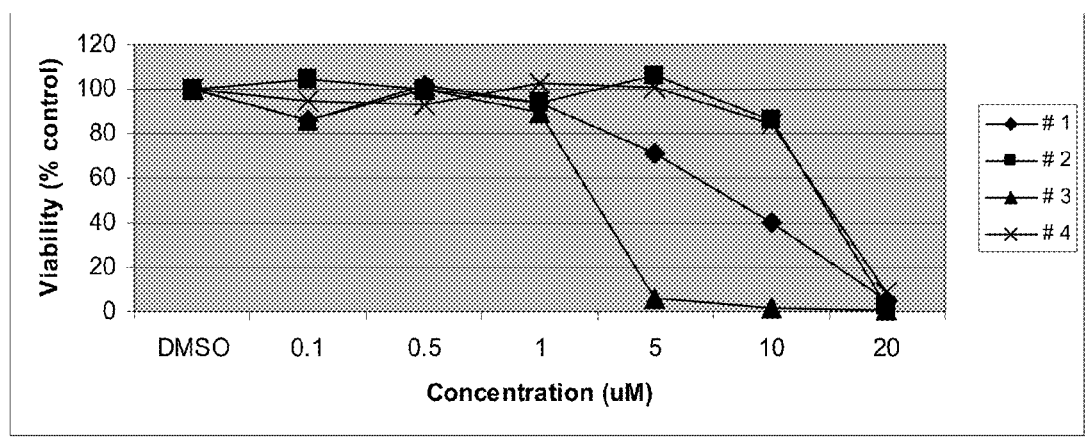
FIG. 5. Viability of A2058 cells treated with BA #1 (diamond), BA #2 (square), BA #3 (triangle) and BA #4 (—X—).
Figure 6:
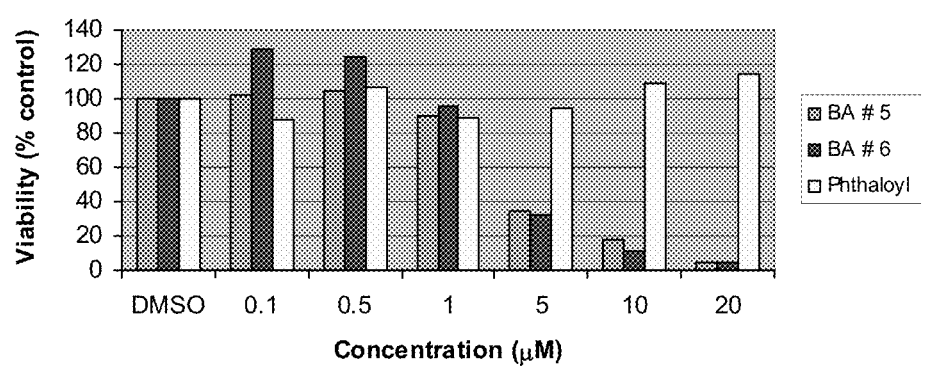
FIG. 6. Viability of A2058 cells treated with BA #5 (grey block), BA #6 (dark block) and phthaloyl derivative (Phthaloyl, white block).
Figure 7:
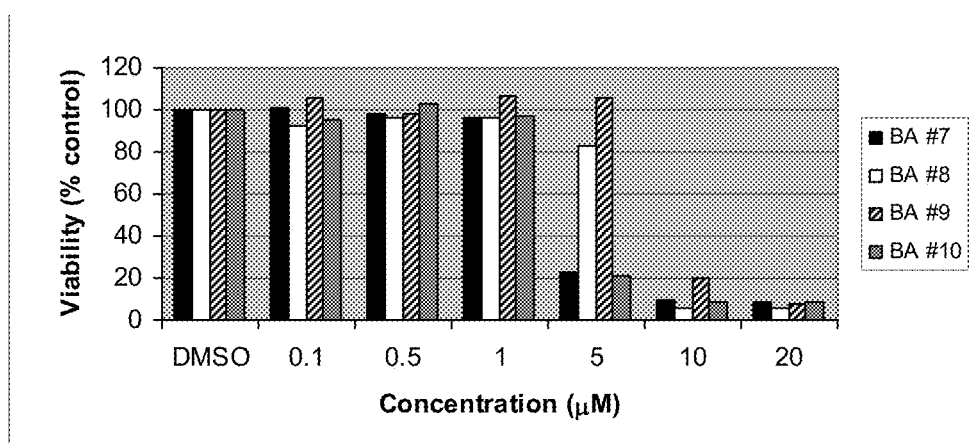
FIG. 7. Viability of A2058 cells treated with BA #7 (dark block), BA #8 (white block), BA #9 (stripe block) and BA #10 (grey block).
Figure 8:
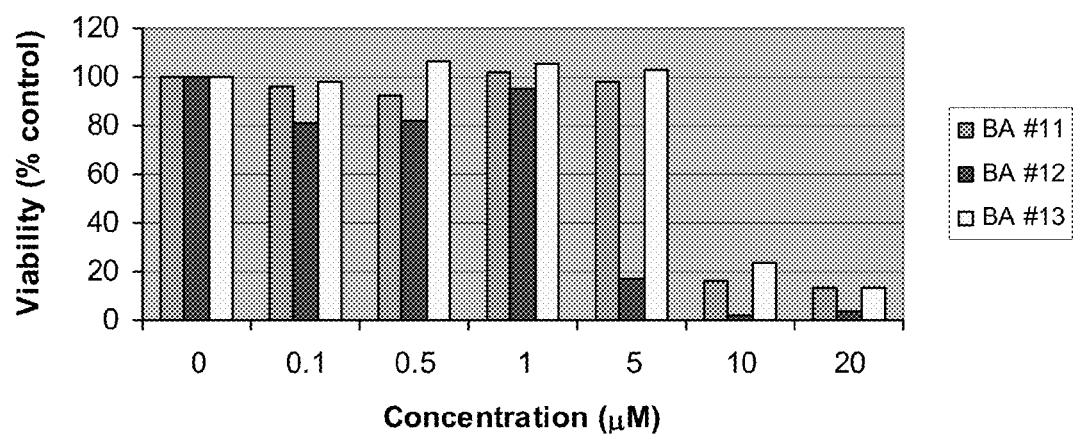
FIG. 8. Viability of A2058 cells treated with BA #11 (grey block), BA #12 (dark block) and BA #13 (white block).

One aspect of the present disclosure related to berbamine derivatives.

Berbamine has a structure as shown below:

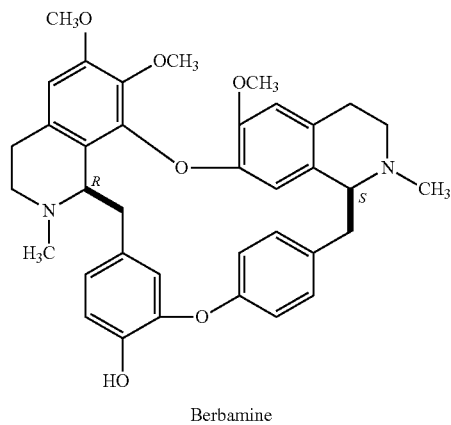

Berbamine

In certain embodiments, a berbamine derivative has a structure comprising Structure A:

Structure A

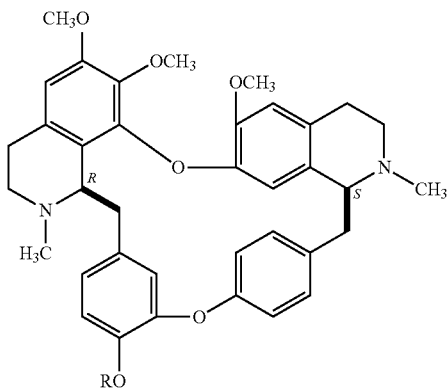

including pharmaceutically acceptable variants thereof, wherein:
  R is selected from the group consisting of —C(=O)—(CH$_2$)$_n$NR'R" and —(CH$_2$)$_n$NR'R";
  R' is selected from the group consisting of H, substituted and unsubstituted alkyl, substituted and unsubstituted aryl, and substituted and unsubstituted acyl groups;
  R" is selected from the group consisting of H, substituted and unsubstituted alkyl, substituted and unsubstituted aryl, and substituted and unsubstituted acyl groups; and
  n is 2, 3, 4, 5, 6, 7, 8, 9, 10, 11, 12, 13, 14, 15, 16, 17, 18, 19, 20, 21, 22, 23, 24, 25, 26, 27, 28, 29 or 30.

In certain embodiments, R' and R" together form a ring structure. In certain embodiments, R' and R" can be the same or different.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene. In certain embodiments, the hydrocarbon group contains 1 to 30 carbons. In certain embodiments, the hydrocarbon group contains 1 to 20 carbons. In certain embodiments, the hydrocarbon group contains 1 to 12 carbons.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl"). Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino and benzothiazolyl.

As used herein, the term "acyl" means R$_1$—C(=O)—, wherein R$_1$ is a substituted or unsubstituted alkyl, or a substituted or unsubstituted aryl group.

As used herein, the term "pharmaceutically acceptable variants" of a compound means variants that retain the biological effectiveness of the compound itself. Examples of pharmaceutically acceptable variants of a compound include, without limitation, pharmaceutically acceptable salts of the compound which are well known to those of skill in the art (e.g. hydrochloride, methanesulfonate, mesylate, maleate, decanoate, enanthate, succinate, lactate, sulfate, and quaternary ammonium salts). Another example of pharmaceutically acceptable variants of a compound is a complex of the compound with nanoparticles wherein the complex is formed via covalent and/or non-covalent interactions among the compound and the nanoparticles.

In certain embodiments, a berbamine derivative has a structure comprising Structure A, wherein:
  n=3;
  R is —(CH$_2$)$_n$NR'R; and
  NR'R" is selected from the group consisting of NH$_2$,

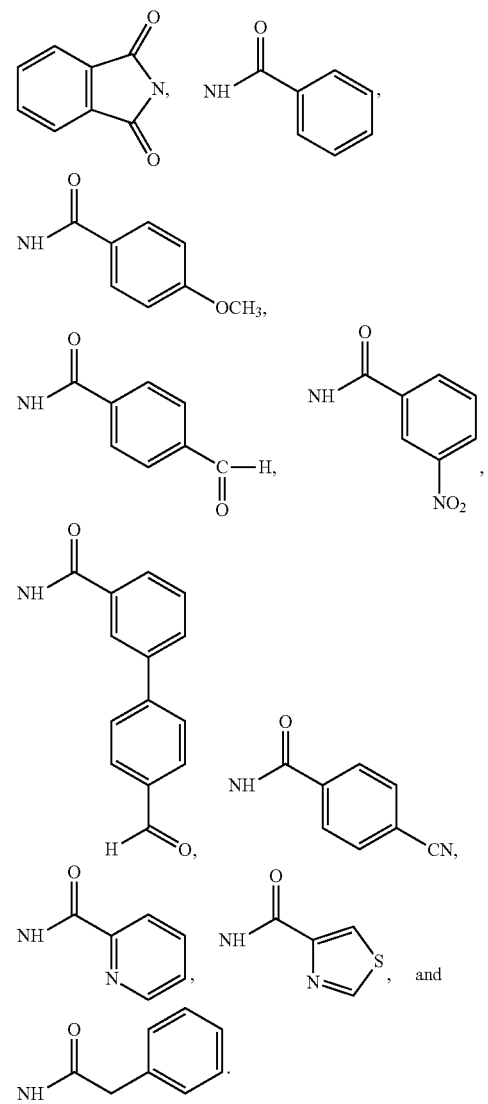

and.

In certain embodiments, a berbamine derivative has a structure comprising Structure A, wherein:
n=2;
R is —C(=O)—(CH$_2$)$_n$NR'R"; and
NR'R" is selected from the group consisting of NH—C(=O)—O—C(CH$_3$)$_3$, and NH$_2$.
Examples of berbamine derivative include, without limitation, BA #1, BA #2, BA #3, BA #4, BA #5, BA #6, BA #7, BA #8, BA #9, BA #10, BA #11, BA #12, and BA #13 as shown below:
BA #1
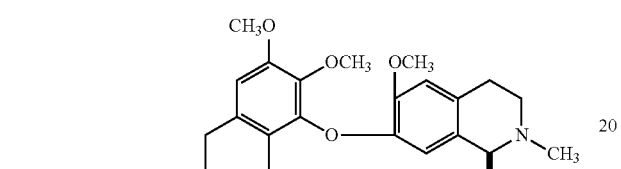
BA #2
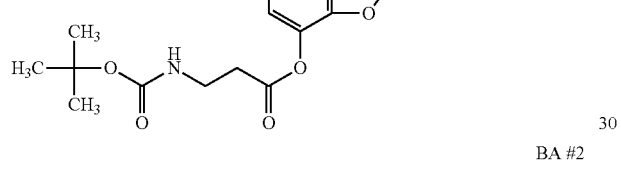
BA #3
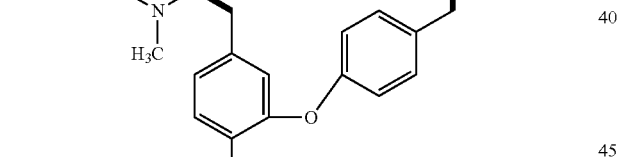
BA #4
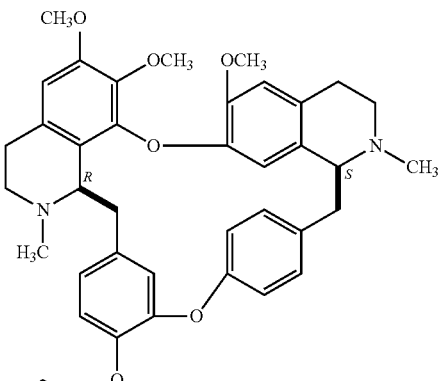
BA #5
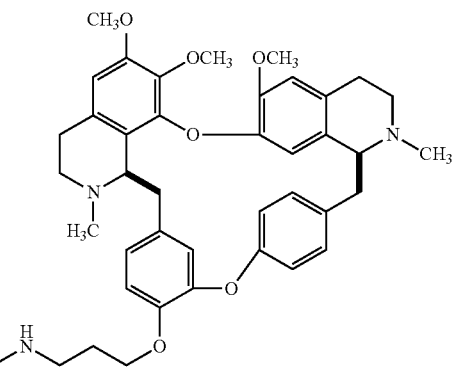
BA #6
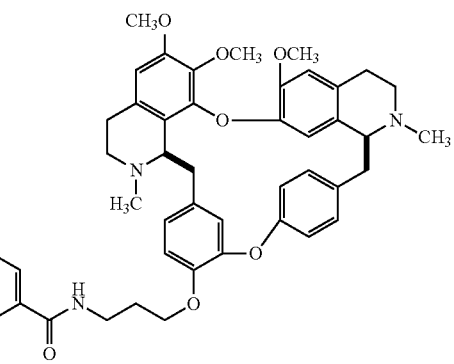
BA #7
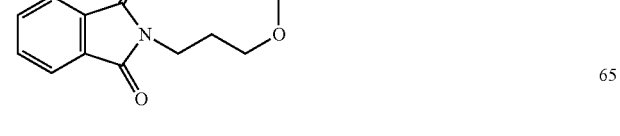
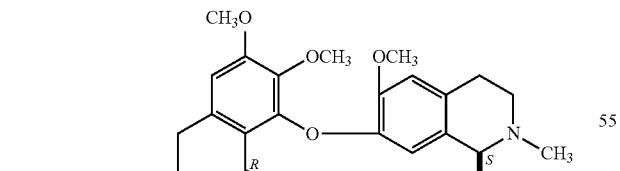

BA #8

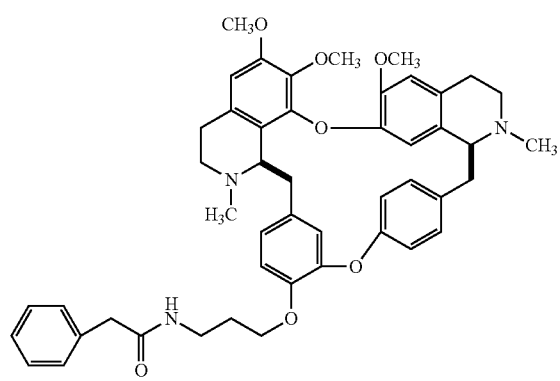

BA #9

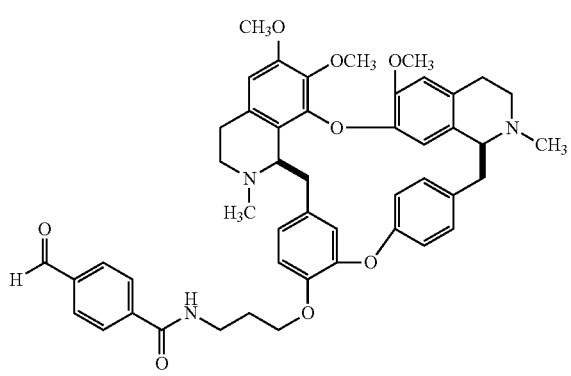

BA #10

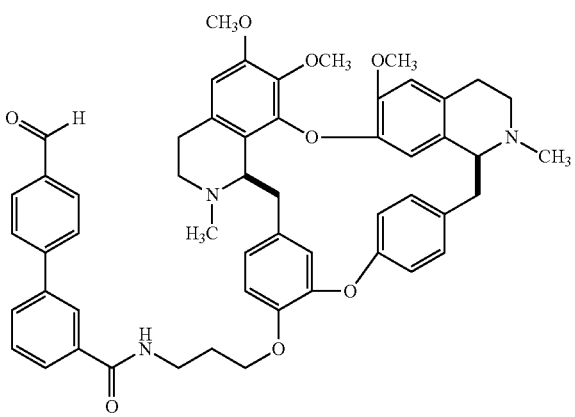

BA #11

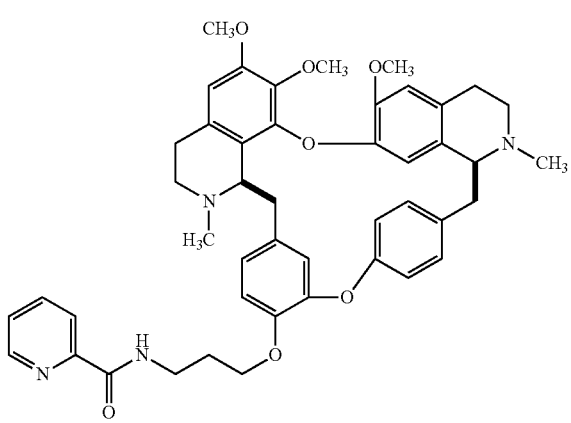

BA #12

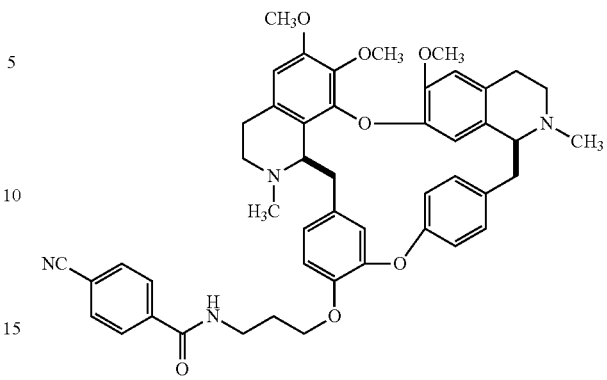

BA #13

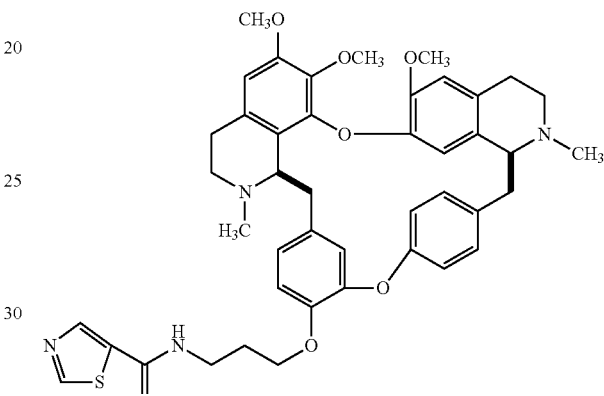

As used herein, the term "phthaloyl derivative" means a compound having the following structure:

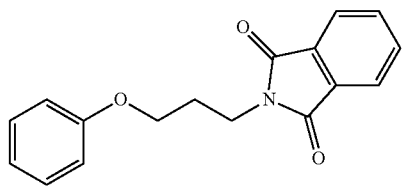

Phthaloyl derivative

As used herein, unless specified otherwise, the term "berbamine amide derivative" means a berbamine derivative having a structure comprising Structure A as described supra, wherein —OR comprises at least one amide functional group. Examples of berbamine amide derivatives include, without limitation, BA #1, BA #3, and BA #5-BA #13.

As used herein, unless specified otherwise, the term "berbamine amine derivative" means a berbamine derivative having a structure comprising Structure A as described supra, wherein —OR comprises at least one amine functional group, and the amine group can be primary amine, secondary amine or tertiary amine group. Examples of berbamine amine derivatives include, without limitation, BA #2 and BA #4

As used herein, unless specified otherwise, the term "berbamine ester derivative" means a berbamine derivative having a structure comprising Structure A as described supra, wherein —OR comprises at least one ester functional group. Examples of berbamine ester derivatives include, without limitation, BA #1 and BA #2.

Another aspect of the present disclosure relates to a pharmaceutical composition comprising at least one berbamine derivative and a pharmaceutically acceptable carrier. In certain embodiments, the pharmaceutical composition may also comprise other known cancer drugs.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a berbamine derivative from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a berbamine derivative, of the formulation and suitable for use in contact with the tissue or organ of a biological system without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. water, acetone and alcohol.

The concentration of berbamine derivative in these formulations can vary widely, and will be selected primarily based on fluid volumes, viscosities, body weight and the like in accordance with the particular mode of administration selected and the biological system's needs. For example, the concentration can be from about 50 mg/kg to about 100 mg/kg, from about 0001% to about 100% wt, from about 0.001% to about 50% wt, from about 0.01% to about 30% wt, or from about 0.1% to about 10% wt. The compositions of the invention can be administered for therapeutic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{-10}$ g to about 100 g, about $10^{-10}$ g to about $10^{-3}$ g, about $10^{-9}$ g to about $10^{-6}$ g, about $10^{-6}$ g to about 100 g, about 0.001 g to about 100 g, about 0.01 g to about 10 g, or about 0.01 g to about 1 g per subject per day. Dosages from about 0.01 mg, up to about 50 g, per subject per day may be used.

Another aspect of the present disclosure relates to a method of treating cancer or tumor using a berbamine derivative, or a composition thereof.

Examples of cancers and tumors include, without limitation, benign tumors, solid tumors, breast cancer, SCCHN, renal cell carcinoma, colon-rectal cancer, oral cancer, lung or other respiratory system cancers, melanoma, skin cancers, uterine cancer, pancreatic cancer, pancreatic adenocarcinoma, liver cancer, prostate cancer, prostate carcinoma, cervical cancer, testicular cancer, genital cancer, bladder cancer, kidney cancer, urinary organs cancers, ovarian cancer, ovarian carcinoma, leukemia (e.g. HTLV-I-dependent leukemia, erythroleukemia, acute lymphoblastic leukemia, acute lymphocytic leukemia, chronic lymphocytic leukemia, acute myelogenous leukemia, megakaryotic leukemia, and large granular lymphocyte leukemia), multiple myeloma, lymphomas (e.g. EBV-related/Burkitt's lymphomas, mycosis fungoides, HSV saimiri-dependent (T-cell) lymphomas, and Hodgkin's disease), blood tumors, and blood and lymphaptic tissues cancers.

Examples of berbamine derivatives have shown stronger activity than berbamine in killing cancer and tumor cells, e.g. prostate cancer (e.g. DU145) cells, melanoma (A2058, A375, G361, SK-MEL-28 and SK-MEL-5) cells, human acute lymphoblastic leukemia (Molt4) cells, human acute lymphocytic leukemia (Reh) cells, imatinib-resistant leukemia (e.g. K562/ADR) cells, multiple myeloma (e.g. U266) cells, human erythroleukemia HEL (homozygous JAK2 V617F mutation) cells, human normal dermal fibroblast (NHDF) cells, ovarian cancer (OVCAR5, SKOV3) cells and pancreatic cancer (PANG-1) cells.

$IC_{50}$ values of examples of berbamine derivatives range from about 1 μM to about 16 μM, while $IC_{50}$ values of berbamine is >20 μM. For example, berbamine derivatives (e.g. BA #3) show significant (at least 10-fold) improvement in activity over berbamine in cancer cell lines tested (e.g. K562/ADR). Berbamine derivatives (e.g. BA #3) also show inhibition of Jak2/Stat3 signaling in cancer cell lines (e.g. A2058, erythroleukemia HEL cells), and show down-regulation of Mcl-1 and Bcl-$x_L$ proteins. Berbamine derivatives (e.g. BA #3) show induction of apoptosis in cancer cell lines (e.g. A2058) and subjects (e.g. mice) treated with berbamine derivatives (e.g. BA #3) do not show significant weight difference comparing to subjects not treated with any berbamine derivatives.

EXAMPLES

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1

Preparation of Berbamine Derivatives

Synthesis of BA #3:

Scheme 1. Synthesis of BA #3.

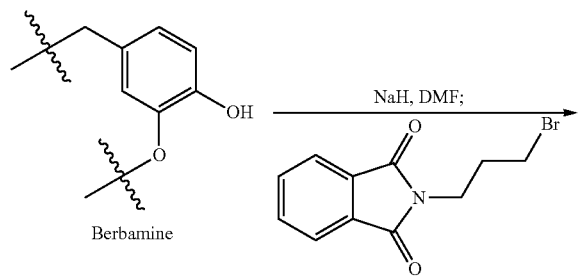

BA #3 can be prepared using a synthesis route as shown in Scheme 1. In one embodiment, berbamine (1 eq) in DMF (0.2M) was added to a suspension of degreased NaH (3 eq) in DMF (0.5M) at 0° C. The obtained suspension was slowly warmed to room temperature, stirred for 2 hours, and cooled to 0° C. Then bromophthalimide (1.5 eq) was added to the suspension, and the reaction mixture was warmed to room temperature and stirred overnight. Saturated aqueous $NH_4Cl$ solution was added to the reaction mixture, and then the reaction mixture was poured into water and extracted with ethyl acetate (3×). The organic layer was washed with water (2×), dried over $MgSO_4$, filtered and concentrated. The crude mixture was purified via $SiO_2$ using 4% $NH_3$/MeOH in dichloromethane (DCM), and the yield was ~50%.

Synthesis of BA #4:

Scheme 2. Synthesis of BA #4.

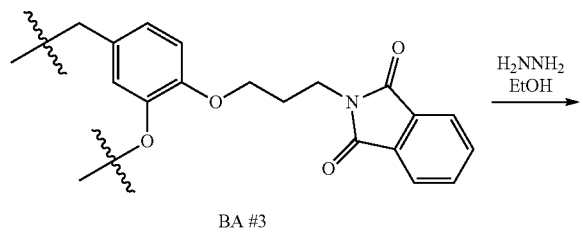

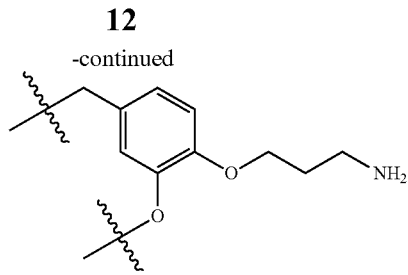

BA #4 can be prepared using a synthesis route as shown in Scheme 2. In one embodiment, hydrazine-hydrate (50 eq) was added to a solution of berbamine-phthalimide (1 eq) in EtOH (0.1M). The obtained reaction mixture was refluxed overnight with stirring. The reaction mixture was then cooled to room temperature and poured into water/DCM. The aqueous layer was extracted 2× with additional DCM, and the combined organic layer was dried over $MgSO_4$, filtered and concentrated. No further purification was needed, and the yield was ~85%.

Synthesis of Berbamine Amide Derivatives (e.g. BA #5-#13):

Scheme 3. Synthesis of berbamine amide derivatives.

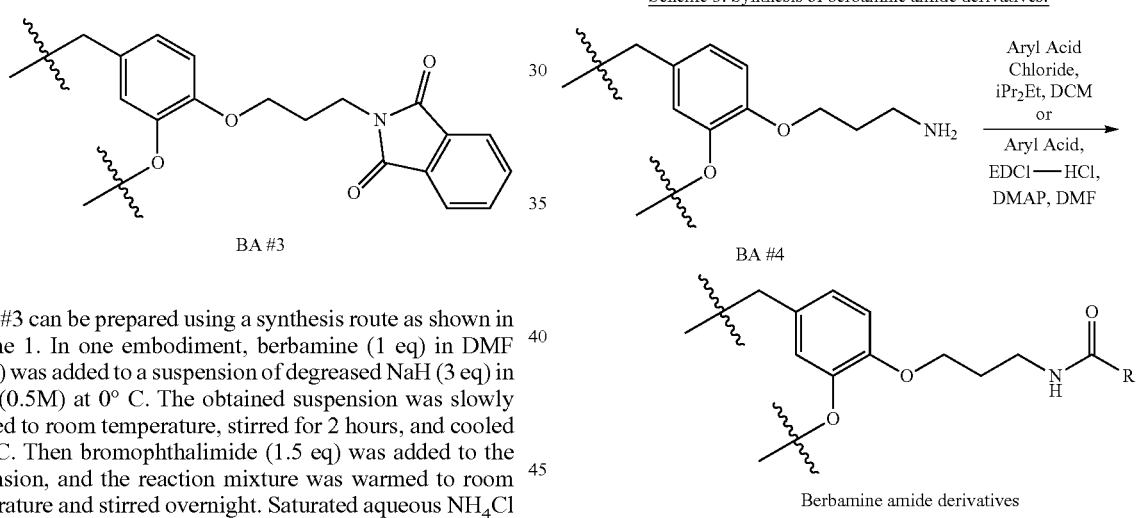

Berbamine amide derivatives

Berbamine amide derivatives can be prepared by reacting a berbamine amine derivative with a desired acid or a desired acid chloride (exemplary synthesis route as shown in Scheme 3). The berbamine amine derivative can be prepared as described supra (exemplary synthesis route as shown in Scheme 2).

In one embodiment, an aryl acid chloride (2 eq) was slowly added to a 0° C. solution of a desired berbamine amine derivative (1 eq) and distilled $NEt_3$ (4 eq) in THF (0.1M). The reaction mixture was warmed to room temperature and stirred overnight. Then, the reaction solution was poured into water and extracted with EtOAc (2×). The combined organic layer was washed with water, dried over $MgSO_4$, filtered, concentrated and further purified via $SiO_2$ using 3% $NH_3$/MeOH in DCM, and the yield was ~50-75%.

In one embodiment, a desired berbamine amine derivative (1 eq), a desired aryl acid (1.5 eq), EDCI-HCl (1.5 eq) and DMAP (0.1 eq) were combined in DMF (0.1M) and stirred at room temperature overnight. The reaction mixture was poured into water and extracted with EtOAc (3×). The combined organic layer was washed with water (2×), dried over MgSO$_4$, filtered, concentrated, and further purified via SiO$_2$ using 3% NH$_3$/MeOH in DCM. The yield was 60-80%.

Synthesis of Berbamine Ester Derivatives (e.g. BA #1 and BA #2)

Berbamine ester derivatives can be prepared by reacting berbamine or a berbamine derivative having a hydroxyl group with a desired acid or acid chloride.

For example, BA #1 was prepared by reacting berbamine with a desired acid in the presence of DCC (Scheme 4). BA #2 was prepared by hydrolysis of BA #1 (Scheme 4).

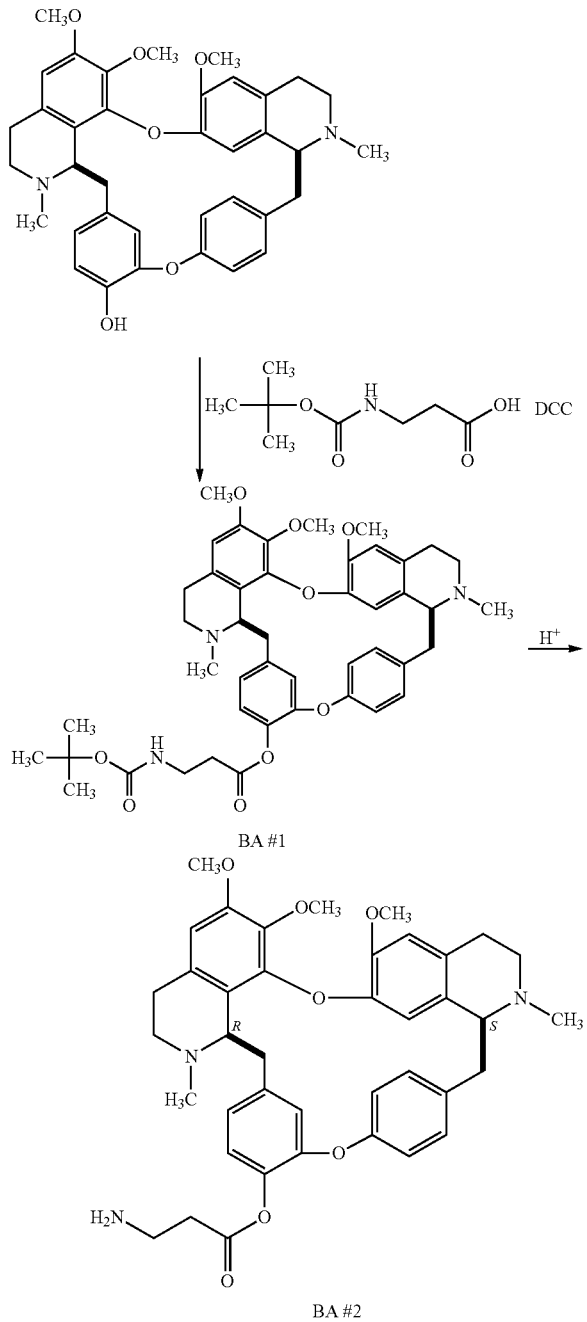

Scheme 4. Synthesis of BA #1 and #2

Example 2

Berbamine Derivatives Showed Lower IC$_{50}$ in DU145 Prostate Cancer Cell Line, A2058 Human Melanoma Cell Line Comparing to Berbamine IC$_{50}$ of values of berbamine derivatives were determined in cancer cell lines DU145 and A2058 respectively. DU145 and A2058 cells (5,000 cells/well) were treated with berbamine derivatives in a dose-dependent manner (0.1 to 20 μM in 1% DMSO for 48 h. Then, MTS assay for cell viability were carried out to determine the IC$_{50}$ values. Four samples were tested for each berbamine derivatives at each concentration in each cell line, and the averaged data were shown in Table 1 and FIGS. 1-8.

TABLE 1

IC$_{50}$ of berbamine derivatives in cancer cell lines DU 145 and A2058

| Test Cell line | DU145 | A2058 |
| --- | --- | --- |
| Berbamine IC$_{50}$ (μM) | >20 | >20 |
| Phthaloyl derivative IC$_{50}$ (μM) | >20 | >20 |
| BA #1 IC$_{50}$ (μM) | 9.4 | 7.4 |
| BA #2 IC$_{50}$ (μM) | 15.2 | 14.6 |
| BA #3 IC$_{50}$ (μM) | 3.4 | 2.9 |
| BA #4 IC$_{50}$ (μM) | 15.5 | 14.3 |
| BA #5 IC$_{50}$ (μM) | 7.9 | 3.9 |
| BA #6 IC$_{50}$ (μM) | 3.5 | 3.4 |
| BA #7 IC$_{50}$ (μM) | 6.9 | 3.5 |
| BA #8 IC$_{50}$ (μM) | 6.6 | 7.1 |
| BA #9 IC$_{50}$ (μM) | 7.7 | 8.1 |
| BA #10 IC$_{50}$ (μM) | 3.7 | 3.4 |
| BA #11 IC$_{50}$ (μM) | 12.3 | 8.3 |
| BA #12 IC$_{50}$ (μM) | 5.6 | 3.3 |
| BA #13 IC$_{50}$ (μM) | 13.6 | 8.2 |

Example 3

Figure 9:
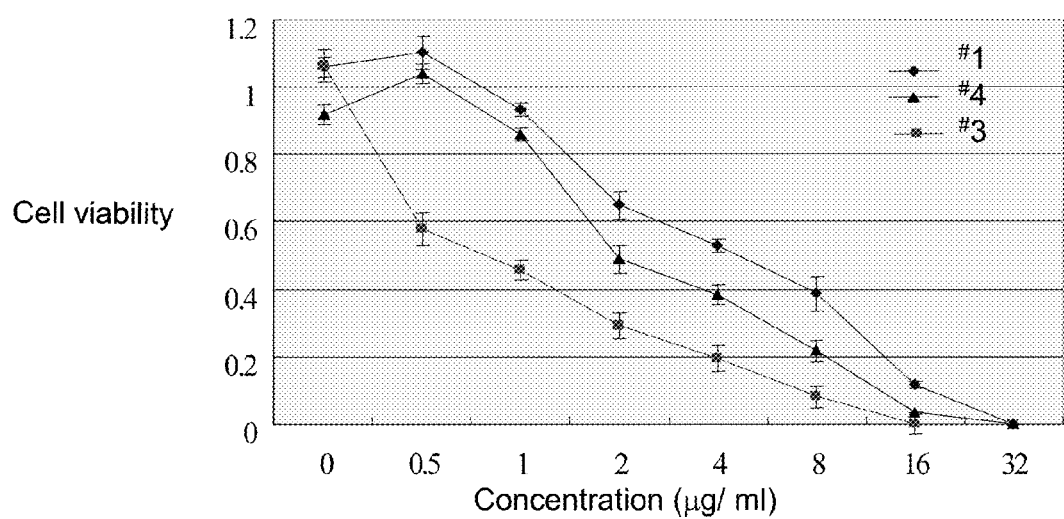
FIG. 9. Viability of K562/ADR cells treated with BA #1 (circle), BA #3 (triangle) and BA #4 (square).

Berbamine Derivatives Showed Lower IC$_{50}$ in Imatinib-Resistant Leukemia (K562/ADR) Cells Comparing to Berbamine Imatinib-resistant leukemia (K562/ADR) cells (5,000 cells/well) were treated with different concentrations (0.6-40 μM in DMSO) of BA #1, BA #3 and BA #4 respectively for 48 hours and cell viability was measured. The results (Table 2, FIG. 9) indicated that berbamine derivatives displayed higher potency to kill K562/ADR cells comparing to berbamine.

TABLE 2

IC$_{50}$ of berbamine derivatives in K562/ADR

|  | Berbamine IC$_{50}$ (μM) | BA #1 IC$_{50}$ (μM) | BA #3 IC$_{50}$ (μM) | BA #4 IC$_{50}$ (μM) |
| --- | --- | --- | --- | --- |
| K562/ADR | 8.9 | 6.4 | 1.1 | 3.0 |

Example 4

Figure 10:
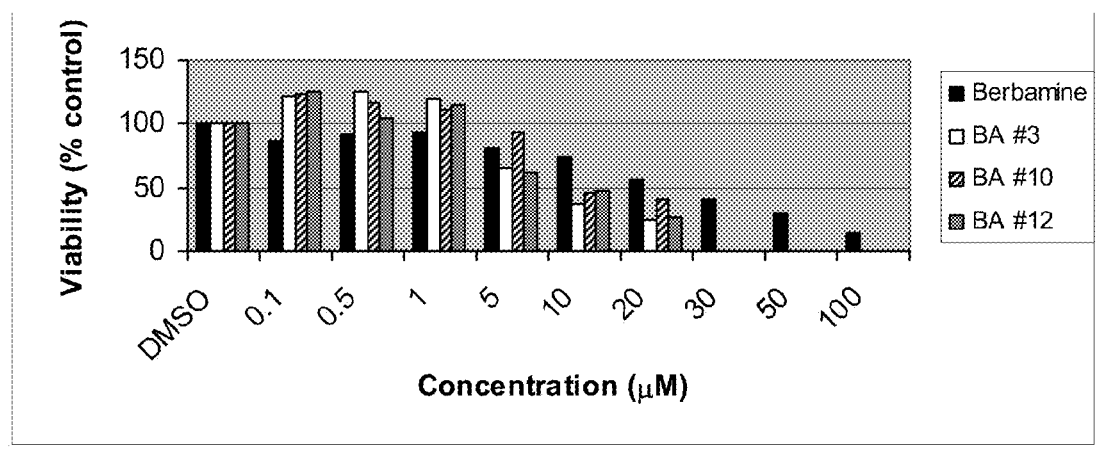
FIG. 10. Viability of human normal dermal fibroblast (NHDF) cells treated with berbamine (dark block), BA #3 (white block), BA #10 (stripe block) and BA #12 (grey block).

Berbamine Derivatives Showed Lower IC$_{50}$ Human Normal Dermal Fibroblast (NHDF) Cell Line and Human Erythroleukemia HEL (Homozygous JAK2 V617F Mutation) Cells Comparing to Berbamine Human normal dermal fibroblast (NHDF) (5,000) cells were treated with different concentration (0.1 μM to 100 μM in 1% DMSO of berbamine, BA #3, BA #10 and BA #12 respectively for 48 hours and cell viability was measured. The results (Table 3, FIG. 10) indicated that berbamine derivatives displayed higher potency to kill NHDF cells comparing to berbamine.

Figure 11:
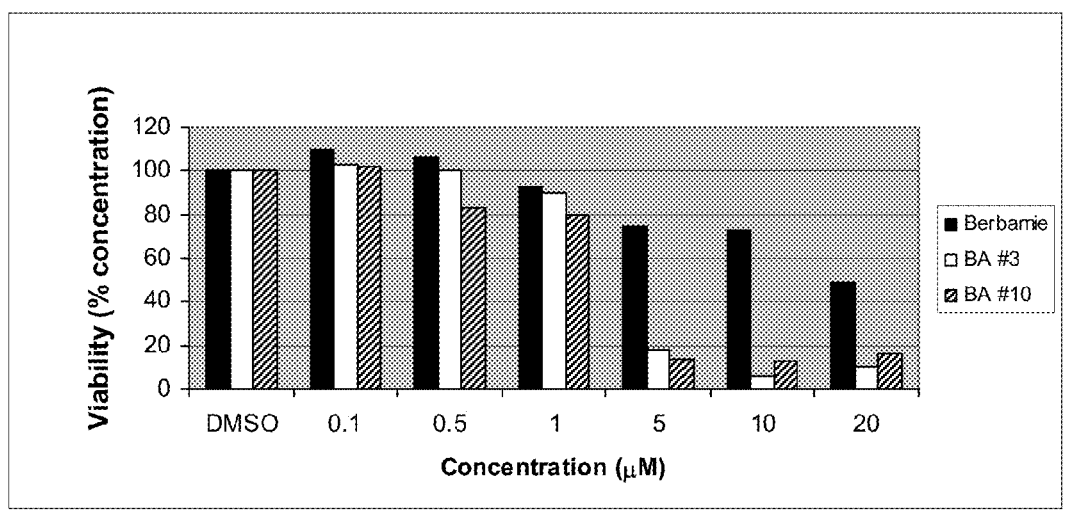
FIG. 11. Viability of human erythroleukemia HEL (homozygous Jak2 V617F mutation) cells treated with berbamine (dark block), BA #3 (white block), and BA #10 (stripe block).

HEL Jak2 V617 mutation cells (10,000 cells/well) were treated with different concentration (0.1 µM to 20 µM in 1% DMSO of berbamine, BA #3, and BA #10 respectively for 48 h. Then, MTS assay for cell viability were carried out to determine the $IC_{50}$ values. Four samples were tested for each test compound at each concentration, and the averaged data were shown in Table 3 and FIGS. 10-11.

TABLE 3

$IC_{50}$ of berbamine derivatives in NHDF cells and HEL cells.

| | Berbamine $IC_{50}$ (µM) | BA #3 $IC_{50}$ (µM) | BA #10 $IC_{50}$ (µM) | BA #12 $IC_{50}$ (µM) |
|---|---|---|---|---|
| NHDF | 24 | 7.5 | 9.4 | 9.2 |
| HEL Jak2 V617 mutation | 19.6 | 3.2 | 2.8 | N/A |

Example 5

Figure 12:
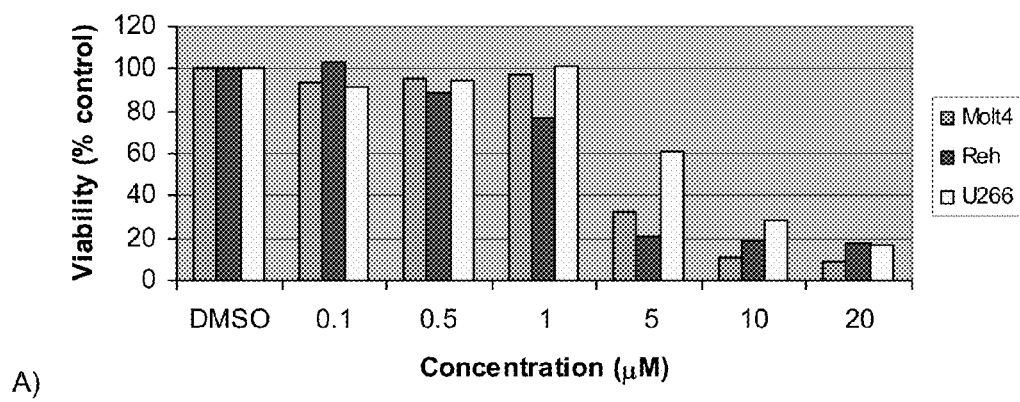
FIG. 12. BA #3 reduced cell viability in cancer cells. A) in human acute lymphoblastic leukemia (Molt4) cells (grey block), human acute lymphocytic leukemia (Reh) cells (dark block), and multiple myeloma (U266) cells (white block); B) in melanoma cells: A375 (dark block), G361 (white block), SK-MEL-28 (stripe block) and SK-MEL-5 (grey block).
Figure 12:
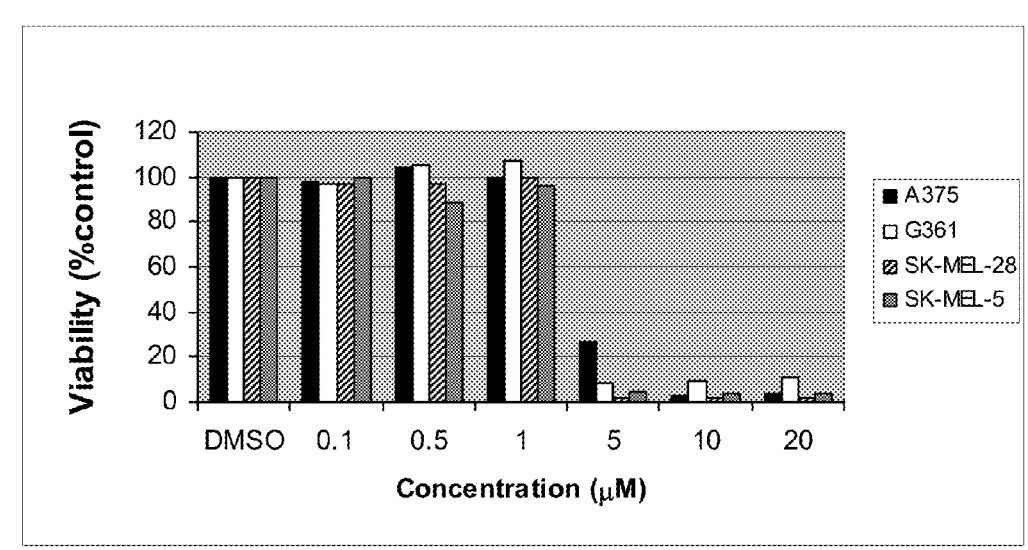
Figure 13:
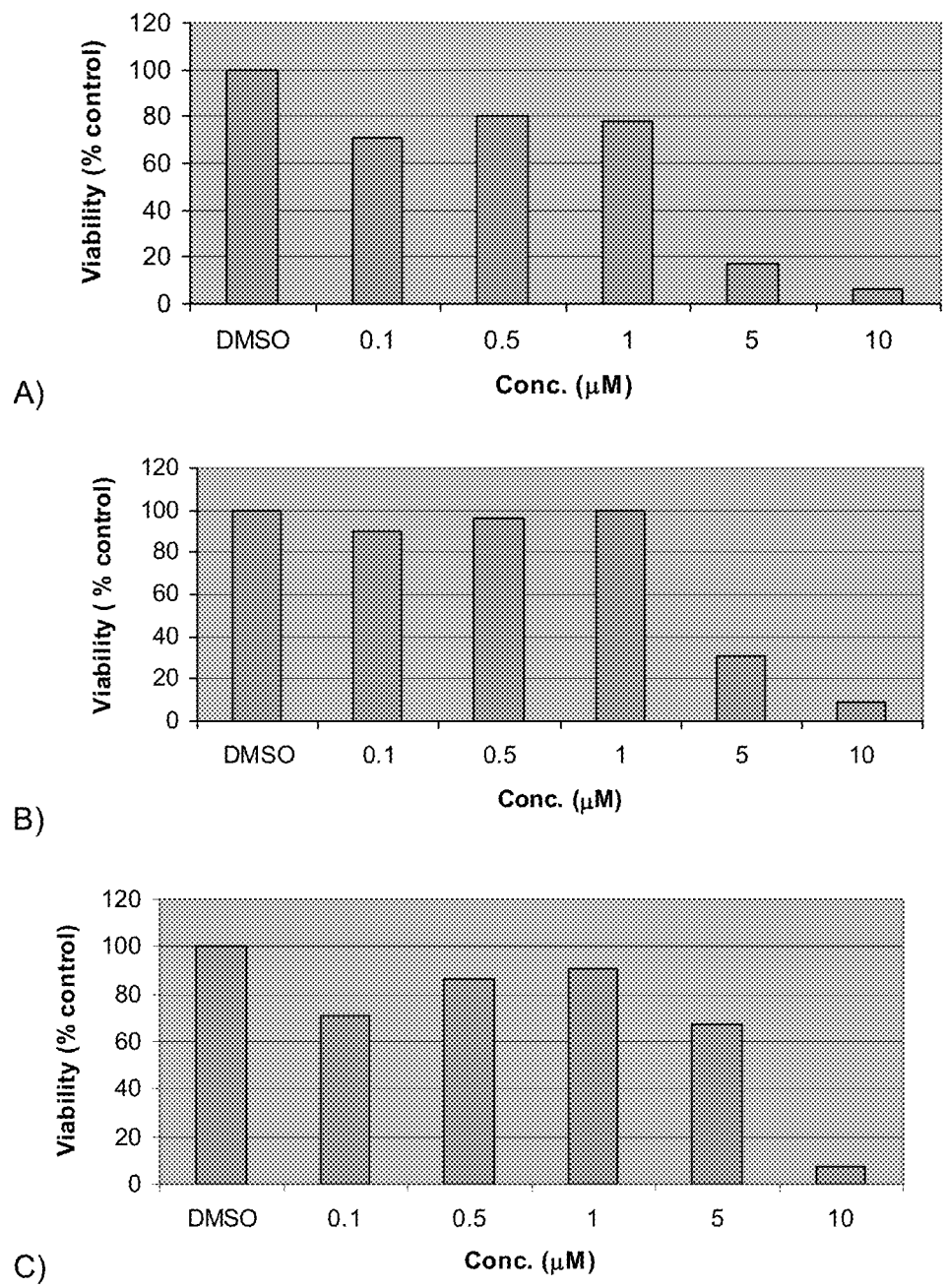
FIG. 13. BA #3 reduced cell viability in cancer cells.

BA #3 Reduced Cell Viability in Human Acute Lymphoblastic Leukemia (Molt4) Cells, Human Acute Lymphocytic Leukemia (Reh) Cells, Multiple Myeloma (U266) Cells, Melanoma (A375, G361, SK-MEL-28 and SK-MEL-5) Cells, Ovarian Cancer (OVCAR5, SKOV3) Cells and Pancreatic Cancer (PANC-1) Cells Each type of cells (5,000 or 10,000 cells/well) were treated with different concentration (0.1 µM to 20 µM in 1% DMSO of berbamine and BA #3 respectively for 48 h. Then, MTS assay for cell viability were carried out to determine the $IC_{50}$ values. Four samples were tested for each test compound at each concentration for each type of cells, and the averaged data were shown in Table 4 and FIGS. 12-13.

TABLE 4

$IC_{50}$ of berbamine and BA #3 in Molt4 cells, Reh cells, U266 cells, A375 cells, G361 cells, SK-MEL-28 cells and SK-MEL-5 cells

| Test cells | Molt4 | Reh | U266 | A375 | G361 | SK-MEL-28 | SK-MEL-5 | OVCAR5 | SKOV3 | PANC-1 |
|---|---|---|---|---|---|---|---|---|---|---|
| $IC_{50}$ (µM) | 3.9 | 2.9 | 6.7 | 3.7 | 3.1 | 3.0 | 3.3 | 2.8 | 3.9 | 6.4 |

Example 6

Figure 14:
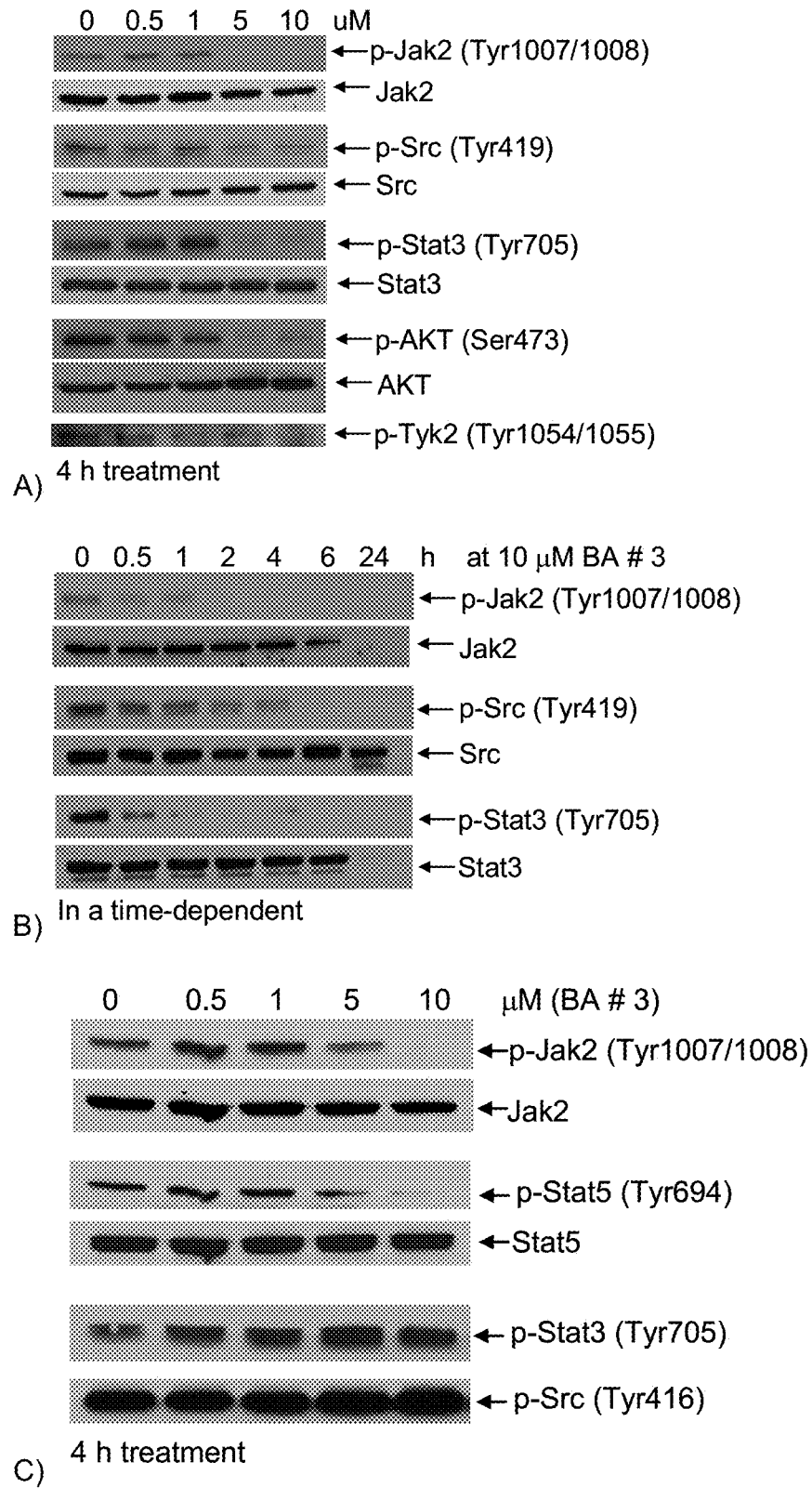
FIG. 14. BA #3 inhibited Jak2/Stat3 signaling: A) in A2058 melanoma cells after 4 hour treatment of different concentrations of BA #3 (0-10 μM); B) in A2058 melanoma cells after different time of treatment (0-24 hour) of 10 μM BA #3; and C) in the erythroleukemia HEL (HEL Jak2 V617F mutation) cells after 4 hour treatment of different concentrations of BA #3 (0-10 μM).
Figure 15:
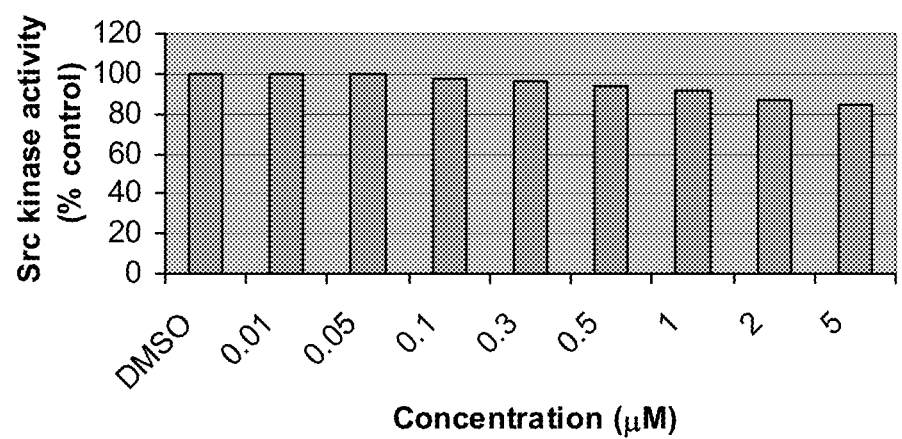
FIG. 15. In vitro Src kinase assay of BA #3.
Figure 16:
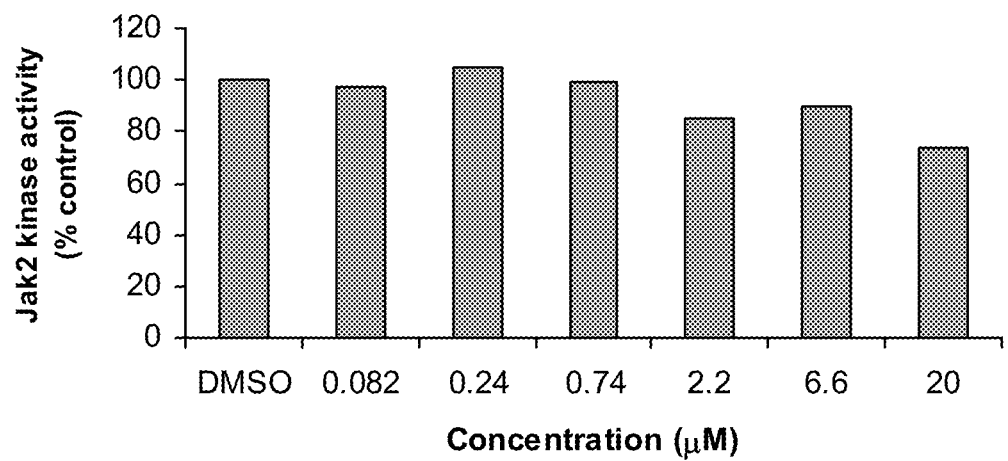
FIG. 16. In vitro Jak2 kinase assay of BA #3.
Figure 17:
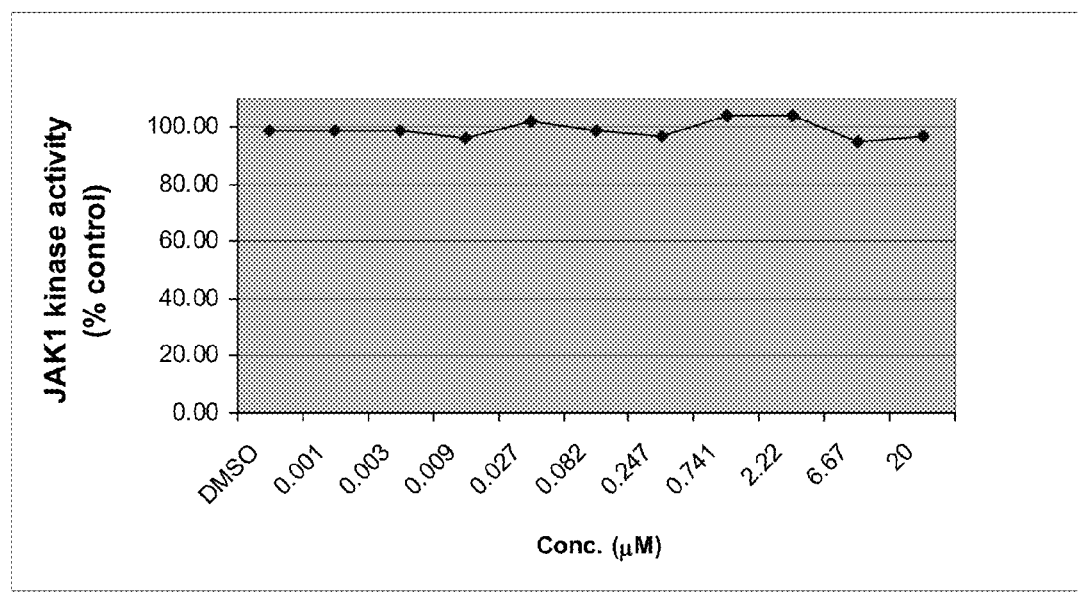
FIG. 17. In vitro Jak1 kinase assay of BA #3.
Figure 18:
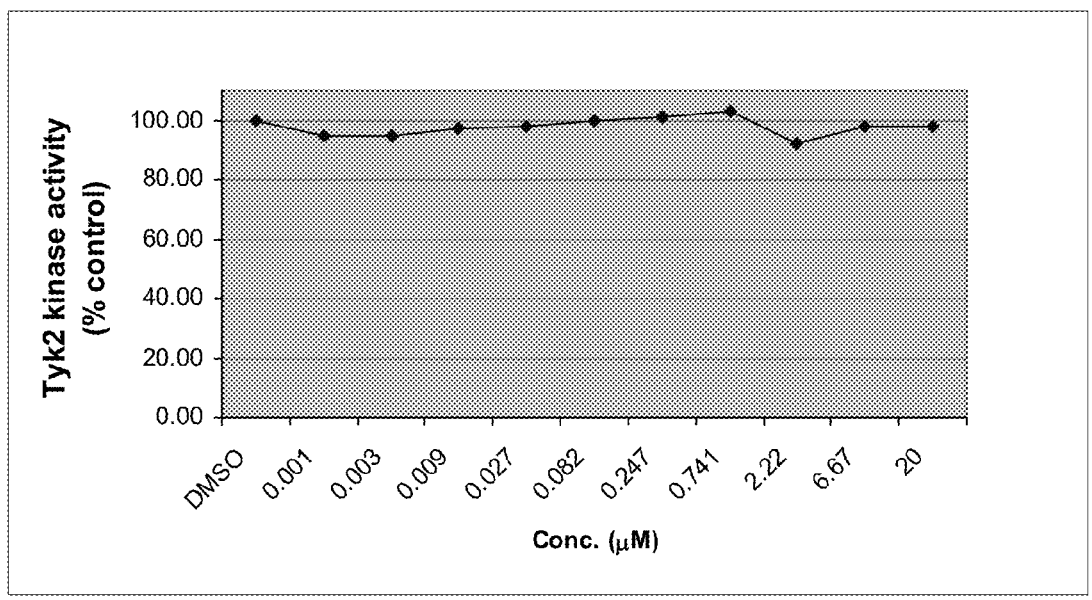
FIG. 18. In vitro Trk2 kinase assay of BA #3.

BA #3 Inhibited Jak2/Stat3 Signaling in A2058 Melanoma Cells and Erythroleukemia HEL Cells BA #3 inhibited Jak2/Stat3 signaling in A2058 melanoma cells (FIGS. 14(A) and (B)) and erythroleukemia HEL cells (FIG. 14(C)). To determine whether BA #3 block Jak2/Stat3 or Src/Stat3 signaling pathway, A2058 melanoma (A and B) and erythroleukemia HEL cells were treated with BA #3 in a dose- or time-dependent manner. Western blots were performed with specific antibodies to p-Jak2, p-Src, p-Stat3, p-AKT, Jak2, Src, Stat3 and AKT. As shown in Figures, BA #3 inhibited phosphorylations of Jak, Src, Stat3 and AKT, indicating BA #3 blocks Jak2/Stat3 or Src/Stat3.

Example 7

BA #3 Reduced Jak2 Autophosphorylation Activities at Tyr1007/1008 Sites in Vitro To determine whether BA #3 inhibits activities of Src kinase, Jak2 kinase, Jak1 kinase and Tyk2 kinase in vitro, activated recombinant proteins were mixed with peptide substrates and ATP in the absence or the presence of BA #3. BA #3 did not inhibit these kinase activities in vitro with substrates (FIGS. 15, 16, 17 and 18). However, BA #3 reduced Jak2 autophosphorylation kinase activity at Tyr1007/1008 sites in vitro in the reaction of mixture of non-activated recombinant Jak2 protein and ATP in the absence of substrates (FIG. 19).

BA #3 did not inhibit activities of Src kinase (FIG. 15), Jak2 kinase (FIG. 16), Jak1 kinase (FIG. 17) and Tyk2 kinase (FIG. 18) with substrates in vitro.

Figure 19:
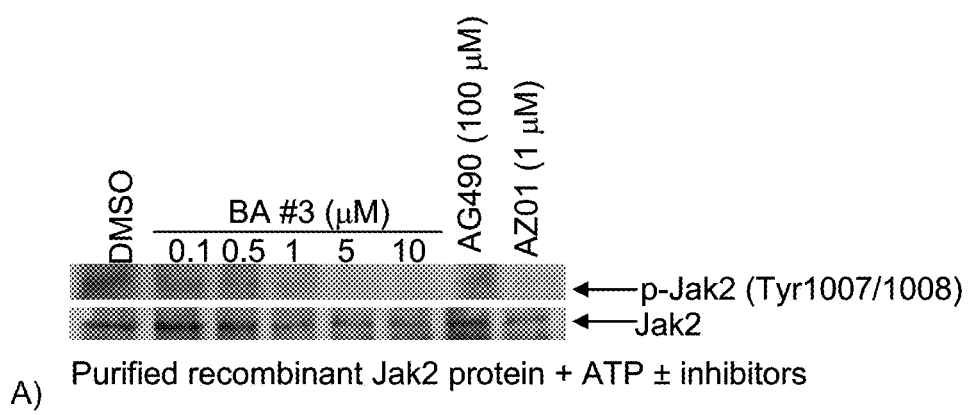
FIG. 19. In vitro Jak2 autophosphorylation kinase assay of BA #3. A) Autophosphorylation of Jak2 at Tyr1007/1008 was required for its catalytic activity, non-activated recombinant Jak2 protein was mixed with ATP in the absence or presence of BA #3; B) inhibitory activity of Jak2 autophosphorylation based on the densitometry of FIG. 19(A).
Figure 19:
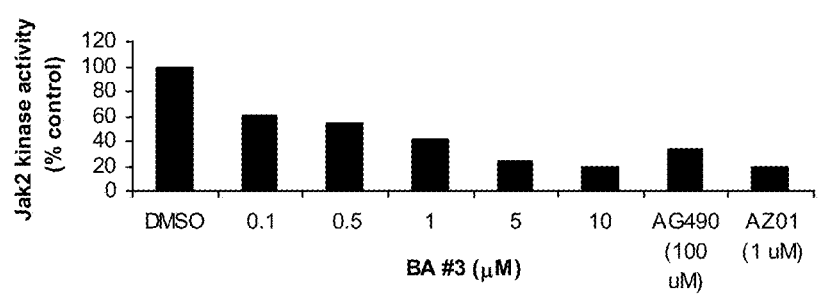

$IC_{50}$ of BA #3 for inhibition of autophosphorylation kinase activity in vitro was 0.69 µM (FIG. 19).

Example 8

BA #3 Down-Regulated Mcl-1 and Bcl-xL Proteins

Figure 20:
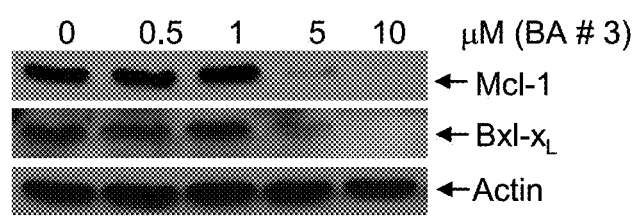
FIG. 20. BA #3 down-regulated Mcl-1 and Bcl-$x_L$ proteins.

To determine whether BA #3 down-regulates Stat3 downstream anti-apototic proteins Mcl-1 and Bcl-xL, cells were treated with BA #3 in a dose-dependent manner for 24 h. Western blots were performed with specific antibodies to Mcl-1 and Bcl-xL. The results showed that BA #3 down-regulated Mcl-1 and Bcl-xL at 5 µM concentration (FIG. 20).

Example 9

BA #3 Induced Apoptosis in A2058 Cells

Figure 21:
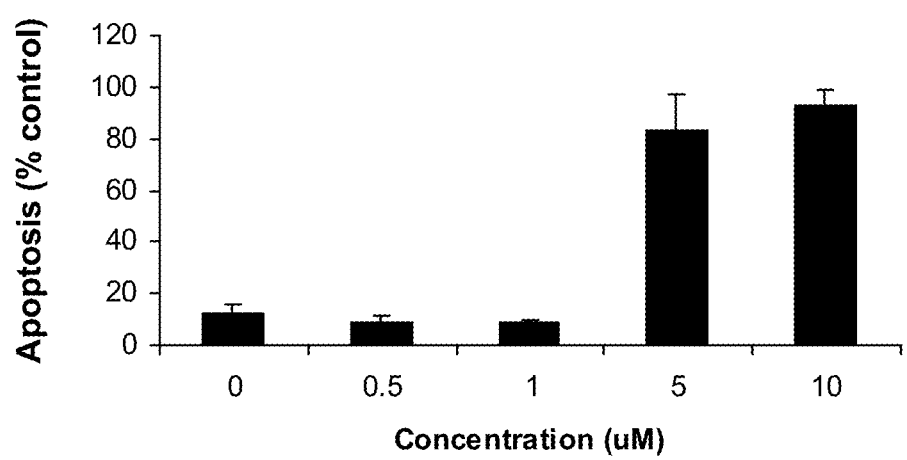
FIG. 21. BA #3 induced apoptosis in A2058 cells.

A2058 cells were treated with BA #3 in a dose dependent manner (0-10 µM) for 48 hours. Apoptosis assay was carried out using Annexin V-FITC, and the results showed that BA #3 induced apoptosis in A2058 cells (FIG. 21).

Example 10

Maximum Tolerated Dose (MTD) Study of BA #3 in Mice

Figure 22:
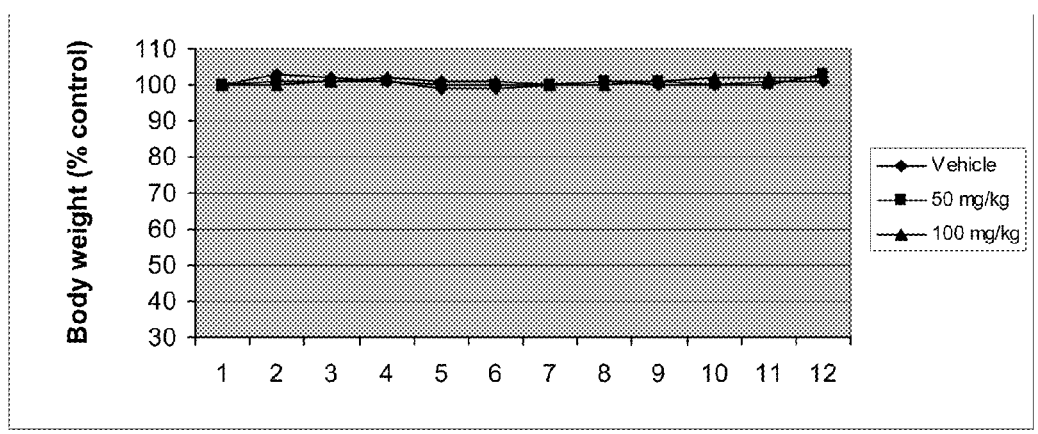
FIG. 22. Maximum tolerated dose (MTD) study of BA #3 on mice. Body weight of mice treated with 50 mg/Kg of BA #3 (square) or 100 mg/Kg of BA #3 (triangle) were compared with body weight of mice treated with vehicle only (diamond). A) and B) are two sets of experiments carried out under the same condition.
Figure 22:
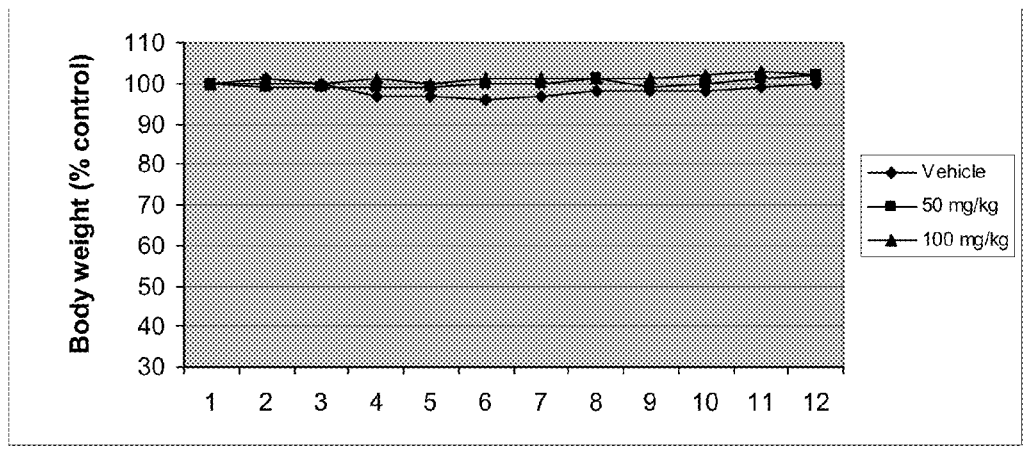
Figure 23:
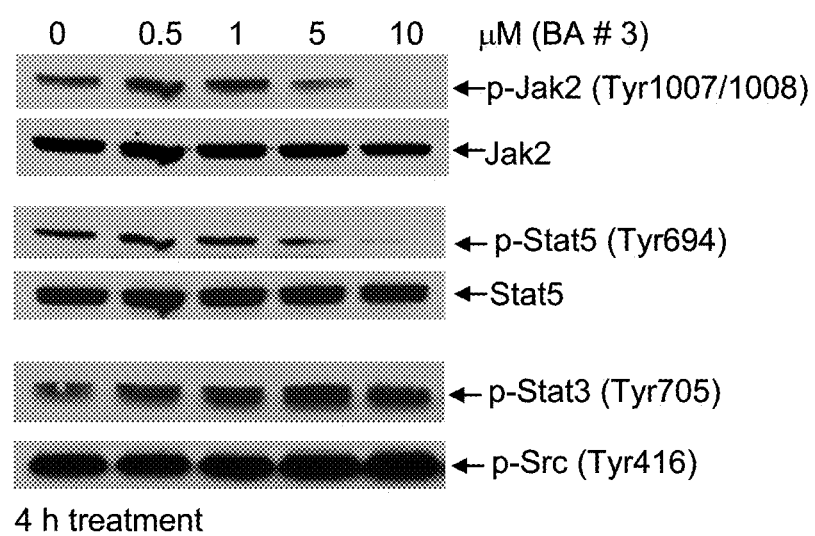
FIG. 23. BA #3 inhibited Jak2/Stat3 signaling in cells after treatment of various concentrations of BA #3 for four hours.

Three test groups of mice (four mice per group) were orally administrated with vehicle only, 50 mg/kg BA #3 and 100 mg/kg BA #3 respectively every day for 5 days. Mice were weighed every day. Two sets of experiments were carried out (FIGS. 22(A) and (B)). The results showed no significant weight differences between the mice treated with vehicle only and the mice treated with BA #3.

The invention claimed is:

1. A compound comprising the following structure of Structure A

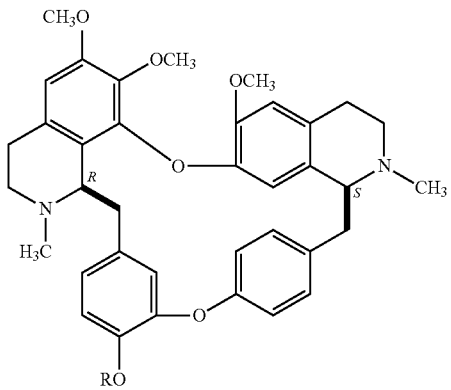

or a pharmaceutically acceptable variant thereof, wherein:
R is selected from the group consisting of —C(=O)—(CH$_2$)$_n$NR'R" and —(CH$_2$)$_n$NR'R";
R' is selected from the group consisting of H, substituted and unsubstituted alkyl, and substituted and unsubstituted acyl groups;
R" is selected from the group consisting of H, substituted and unsubstituted alkyl, and substituted and unsubstituted acyl groups;
n is 2, 3, 4, 5, 6, 7, 8, 9, 10, 11, 12, 13, 14, 15, 16, 17, 18, 19, 20, 21, 22, 23, 24, 25, 26, 27, 28, 29, or 30; and
when n is 2, and R is —(CH$_2$)$_n$NR'R", at least one of R' and R" is not H.

2. A pharmaceutical composition comprising a compound according to claim 1 and a pharmaceutically acceptable carrier.

3. A method of treating cancer and tumor comprising administering a therapeutically effective amount of a pharmaceutical composition comprising a compound according to claim 1.

4. The method according to claim 3, wherein the cancer and tumor is selected from the group consisting of benign tumor, solid tumor, breast cancer, colon-rectal cancer, oral cancer, lung cancer, respiratory system cancers, melanoma, skin cancers, uterine cancer, pancreatic cancer, liver cancer, prostate cancer, cervical cancer, testicular cancer, genital cancer, bladder cancer, kidney cancer, urinary organs cancers, ovarian cancer, leukemia, acute lymphoblastic leukemia, acute lymphocytic leukemia, erythroleukemia, multiple myeloma, blood cancer, and lymphatic tissues cancer.

5. The method according to claim 4, wherein the compound has a structure selected from the group consisting of BA #1, BA #2, BA #3, BA #4, BA #5, BA #6, BA #7, BA #8, BA #9, BA #10, BA #11, BA #12, and BA #13:

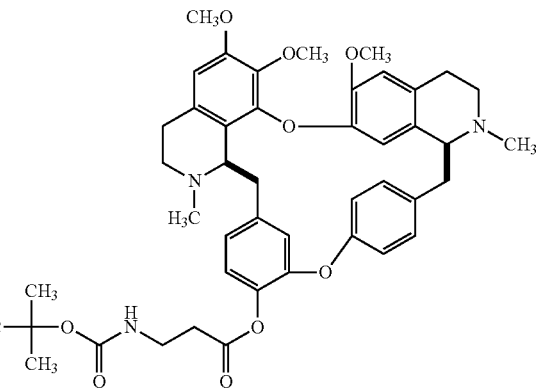

BA #1

BA #2

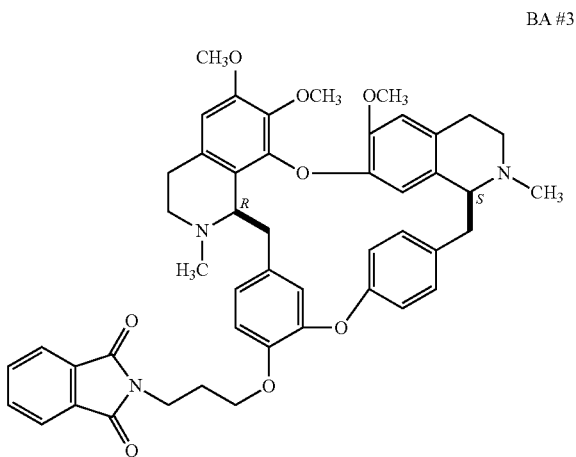

BA #3

BA #4
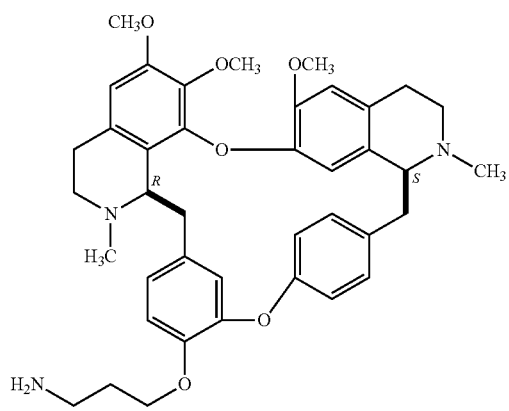
BA #5
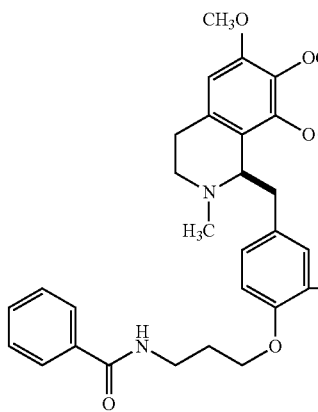
BA #6
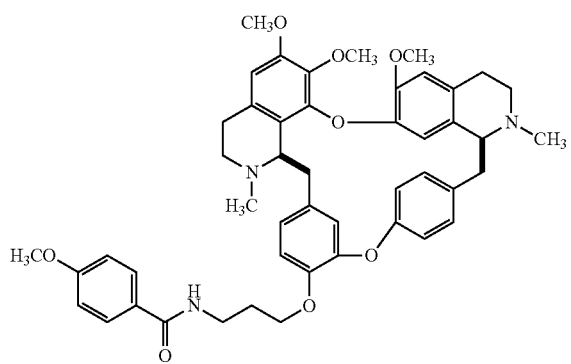
BA #7
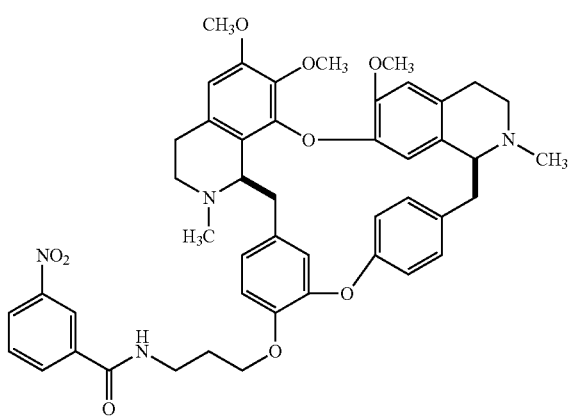
BA #8
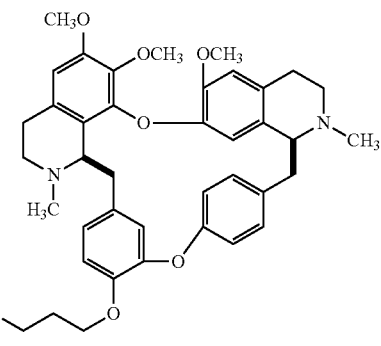
BA #9
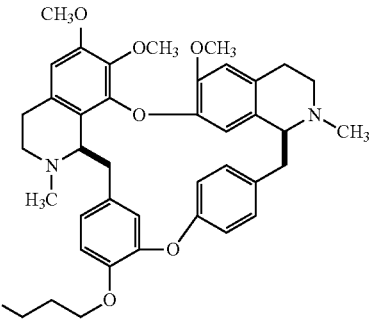
BA #10
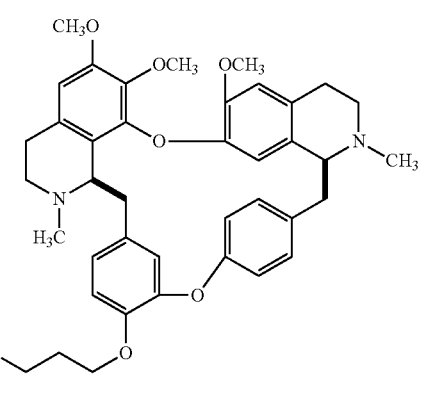
BA #11
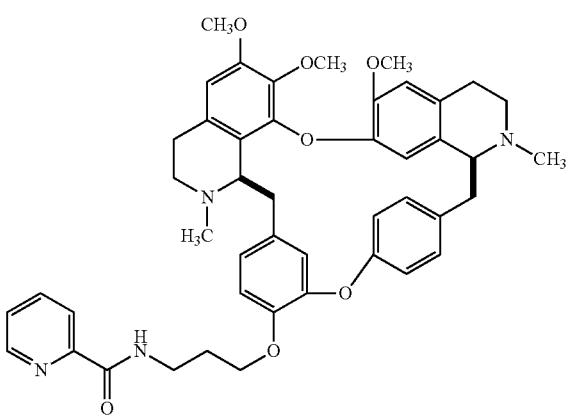

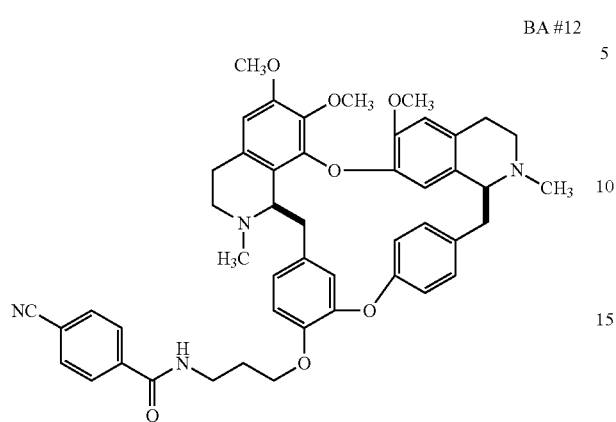
BA #12
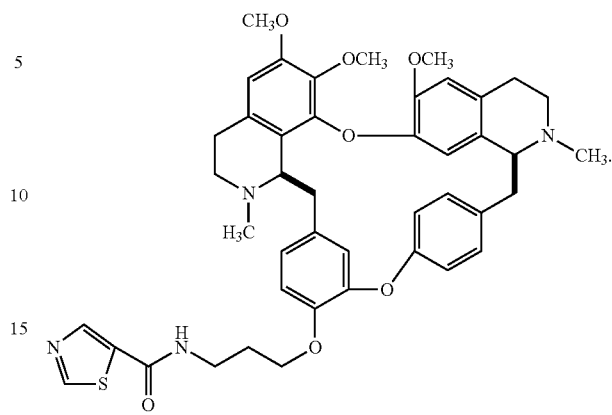
BA #13
* * * * *